United States Patent [19]
Barringer

[11] 3,961,187
[45] June 1, 1976

[54] REMOTE SENSING OF MARINE HYDROCARBON SEEPS

[75] Inventor: Anthony Rene Barringer, Willowdale, Canada

[73] Assignee: Barringer Research Limited, Rexdale, Canada

[22] Filed: Nov. 1, 1974

[21] Appl. No.: 520,527

[30] Foreign Application Priority Data
Nov. 6, 1973   United Kingdom............... 51428/73

[52] U.S. Cl................................ 250/301; 250/253; 250/461 B
[51] Int. Cl.²........................................ G01N 21/38
[58] Field of Search ........... 250/301, 461, 253, 302, 250/372, 458

[56] References Cited
UNITED STATES PATENTS

| | | | |
|---|---|---|---|
| 3,663,814 | 5/1972 | Madsen.......................... | 250/461 X |
| 3,736,428 | 5/1973 | Monroe ............................. | 250/253 |
| 3,783,284 | 1/1974 | McCormack ...................... | 250/301 |
| 3,839,639 | 10/1974 | Hughes .............................. | 250/302 |

*Primary Examiner*—Archie R. Borchelt
*Attorney, Agent, or Firm*—Rogers, Bereskin & Parr

[57] ABSTRACT

A method of determining the presence of hydrocarbon seeps in the sea from an aircraft or other moving vehicle wherein an intense beam of light from an artificial source such as a laser is directed towards the sea and reflections and/or bioluminescence attributable to said beam occurring in the near surface of the sea are observed in the vehicle. Means is provided for discriminating between responses attributable to reflections from the surface of the sea and reflections and/or bioluminescence occurring below the surface of the sea.

5 Claims, 3 Drawing Figures

REMOTE SENSING OF MARINE HYDROCARBON SEEPS

This invention relates to a method of detecting submarine hydrocarbon gas seeps escaping from the ocean floor for use in hydrocarbon exploration.

It is well known that submarine oil and hydrocarbon gas deposits are very commonly accompanied by seepages of oil and gas which gradually appear on the surface of the water. Such seepages appear to be channelled along fractures and microfractures in the overlying rocks and vary in size from microseeps in which very small traces of gases escape to large scale seeps which are obvious to the naked eye. Although seepages of both gas and oil can occur, gas seepages tend to be more common due to the higher mobility of gas and due to the fact that most oil fields are usually associated with at least some hydrocarbon in gaseous form. In some cases gas seeps can be of such major dimensions that streams of bubbles can readily be observed rising to the surface and can be spotted by subtle changes in aerial photographs and by visual observation from aircraft. However, a high proportion of the seeps generate bubbles at a sufficiently slow rate that most if not all of these become dissolved in the sea before reaching the surface of the ocean. This is particularly the case where water depths amount to several hundred feet or greater. Heretofore the dissolved hydrocarbon gases have been measured by sampling the surface water, the measurements being effected in surface vessels. Such measurements are slow and expensive.

The present invention provides a method and apparatus for detecting the presence of such hydrocarbon gases remotely, e.g. from an aircraft or a boat, and enables such measurements to be made rapidly and at relatively low cost compared with conventional techniques.

It has been discovered that frequently gas seeps are accompanied by increased optical scattering in the water and also by an increased concentration of micro-organisms growing in the water. The most common gas to seep from the sea floor is methane which provides an excellent nutrient for certain types of bacteria existing in the sea. These bacteria multiply rapidly and in turn provide an increased supply of nutrients for secondary growths of organisms that cannot be supported by methane alone. Similarly, higher hydrocarbons such as ethane, propane and butane also provide nutrients for some types of micro-organism. The overall effect is to substantially increase the population of a broad variety of bacterial strains as well as other micro and macro-organisms.

In the preferred embodiment of the invention an intense beam of light such as that generated by a laser is pointed downwards from an over-flying aircraft. This beam of light preferably is pulsed, although a continuous source of light could be used with somewhat lesser effectivity. The wavelength of light chosen preferably is in the blue or ultraviolet in order to achieve maximum sensitivity to scattering in the water and to also stimulate bioluminescence in suspended micro-organisms.

The phenomenon of light-initiated bioluminescence is best activated by a light having wavelengths shorter than 4,500 microns in the blue spectrum and is particularly effective in the ultraviolet at a wavelength shorter than 3,500 A. The light emitted by a nitrogen laser at 3371 A is well suited for initiating bioluminescence in many types of marine organism.

The signal returned from the sea from a downward looking light beam can be measured through a narrow band filter at the same wavelength as that of the emitting source in order to monitor turbidity and scattering, and the bioluminescence emission can also be measured at a longer wavelength such as 4,900 A where peak luminescence emission tends to occur. Reflections from the surface can be separated from sub-surface reflections by conventional electronic techniques such as range gating, etc. It is an important feature of the present invention that such surface and sub-surface reflections be separated, because the surface reflections may be attributable to hydrocarbon slicks due to pollution, plankton, etc. instead of hydrocarbon seeps.

Although as stated above a continuous source of light could be used, it is advantageous to employ a pulse source having very short pulse lengths. Thus in the case of a nitrogen laser having a pulse length of at least as short as ten nanoseconds and preferably one nanosecond, the reflection and the scattering from the immediate surface of the ocean as seen at the emitting wavelength, may if desired be gated out in the receiver or otherwise eliminated, and the intensity of the scattered light from immediately below the surface of the sea can be monitored. Thus it is possible to make remotely, highly sensitive measurements of abnormal turbidity caused by high concentrations of gas bubbles or local accumulations of micro-organisms within the sea itself. In the case of bioluminescence phenomena it is possible to differentiate between bioluminescence at the immediate surface of the sea and sub-surface bioluminescence. This may be useful in separating luminescence associated with pulluting oil slicks from underlying micro-organism activity associated with gas seeps.

As used herein, the term "primary light radiation" refers to light generated in the aircraft or other vehicle which is produced by an artificial source such as a laser, and the term "secondary light radiation" refers to light which emanates from sub-surface zones of the sea and which is attributable to reflections and/or bioluminescence in said zones resulting from the primary light radiation.

Figure 1:
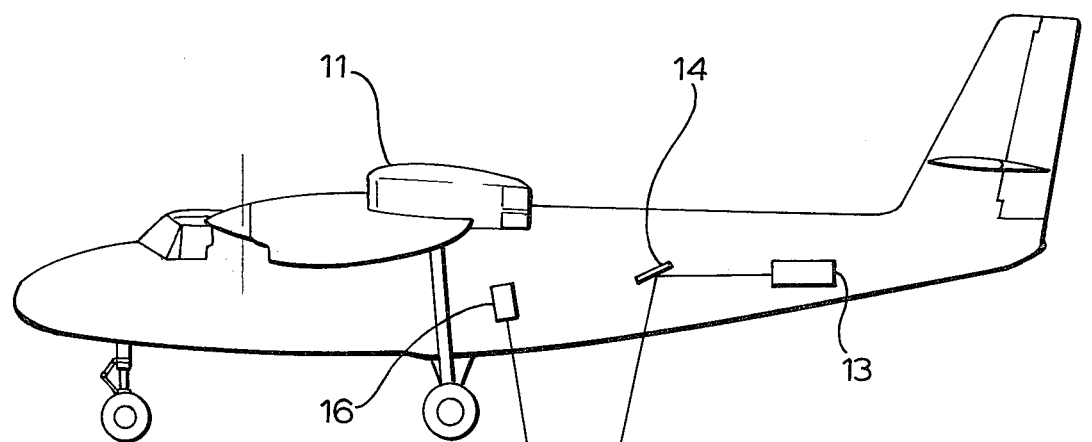
FIG. 1 is a diagrammatic view showing an aircraft carrying out a survey according to the invention.
Figure 2:
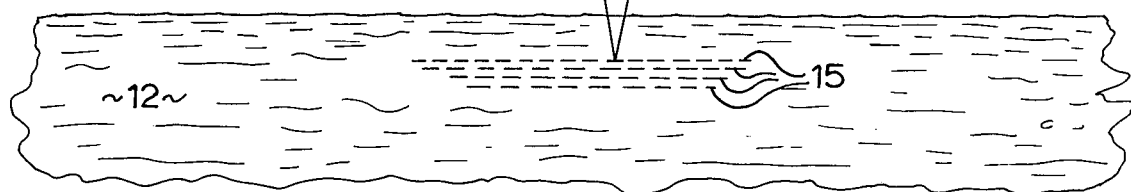
FIG. 2 is a block diagram of apparatus for use in connection with the present invention.

Referring to the drawings, apparatus for use with the invention may be installed in an aircraft 11 flying over the sea 12 preferably at low altitude of approximately 60 meters. Light from a pulsed laser system 13 is reflected from mirror 14 down to the surface of the sea where it penetrates through to layers of scattering 15 lying beneath the surface. Such layers of scattering which are associated with increased microbiological activity and the presence of gas bubbles, reflect the light back through a telescopic receiving system 16. Referring to FIG. 2, the receiving system 16 consists of a telescope 17 directing the received light onto a photomultiplier amplifier assembly 18 whence it is passed to an amplifier 18a the output of which is fed to a cathode ray tube oscilloscope 19. The oscilloscope 19 is triggered from laser system 13 and its sweep has a repetition rate that is tied synchronously to the outgoing pulses from the laser system 13. The face of the oscilloscope 19 can be photographed continuously by means of a strip camera in order to produce a permanent record of the intensity of observed surface reflections.

Figure 3:
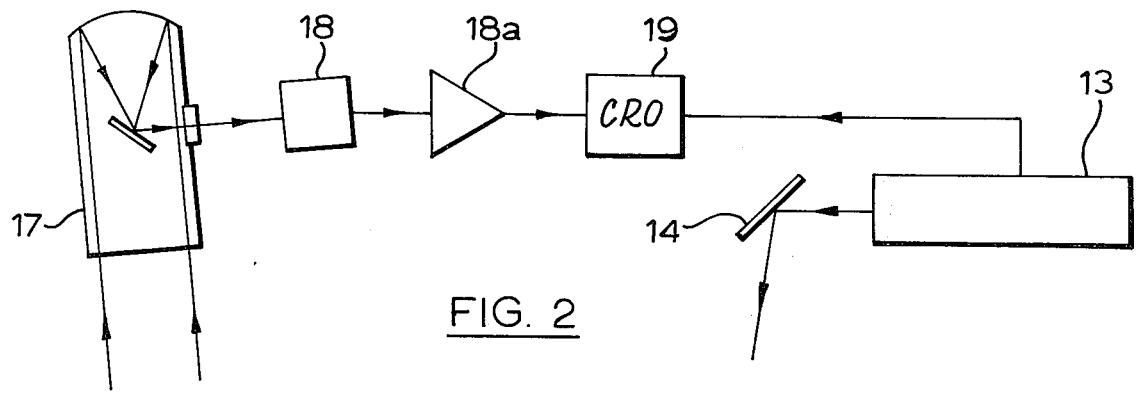
FIG. 3 is a block diagram showing a variant of the apparatus shown in FIG. 2.

A second trace can be displayed on the oscilloscope 19 by splitting the outcoming beam from the telescope into two portions. This is illustrated in FIG. 3 where the output from the oscilloscope 19 is split at a dichloric mirror 20 into two portions, one wavelength being that of the laser system 13 and the other being a longer wavelength representing bioluminescence. These two separate wavelength positions are separately led to photomultipliers 21 and 22. The outputs of these photomultipliers may be connected to a dual trace oscilloscope, or for convenience in recording, on two separate oscilloscopes. The respective parts of the said oscilloscopes may be photographed continuously.

The purpose of the oscilloscope display is to allow the signal received from the sea water surface to be differentiated from sub-surface scattering and bioluminescence. This can be readily observed on the oscilloscope face and photographed. However, it will be appreciated that more sophisticated forms of recording can be employed. These include digital recording methods in which the received signal can be scanned and recorded digitally. This has the advantage of providing much greater dynamic range in the recording and allowing various types of signal processing to be employed to maximize the signal-to-noise ratio of the system. Furthermore, it is possible electronically to scan the signal and to carry out more sophisticated signal processing in real-time if this is so desired.

In a typical survey operation for locating potential oil field target areas, parallel traverses over the sea are flown at fixed intervals such as one or two miles. This survey height may be as low as 60 meters in order to maximize the signal strength; however, higher altitudes may be possible depending upon the strength of the light source. Navigation is carried out by electronic means such as doppler radar, inertial navigation or other suitable conventional techniques.

The aircraft position is recorded during flight along with the data described above such that the two can subsequently be synchronized together. The location of anomalous sub-surface zones of turbidity and bioluminescence eventually are plotted on maps of the survey area.

The images then may be analyzed to locate target areas for subsequent follow-up with marine seismic surveys. The objective is to use the method and apparatus of the invention to cover large areas at relatively high speed and low cost so that the much more costly and slower seismic techniques can be applied initially to areas of high priority selected from the sweep survey.

The depth of penetration of the light beam into the sea is a function inter alia of the wavelength and intensity of the light and the turbidity of the sea. For wavelengths of the ultra-violet range, a penetration of about 10 cm. is an approximate useful working limit; for wavelengths in the visible range, the penetration of the beam would be of the order of 2 meters. It will be understood, of course, that the above referred to penetration depths are approximations only and do not constitute exact limits.

What I claim is:

1. A method of determining the presence of hydrocarbon seeps in the sea, comprising:
   a. traversing an area of the sea in a moving vehicle,
   b. generating a beam of primary light radiation and directing said light beam towards the sea, said beam being of sufficient intensity and of such wavelength composition to produce secondary light radiation in subsurface zones of the sea, said secondary radiation being observable in the vehicle, said zones being located near the surface of the sea,
   c. receiving secondary light radiation emanating from said zones, and separating said received secondary light radiation into a first component attributable to radiation emanating from beneath the surface of the sea and a second component comprising the remainder of the received radiation,
   d. determining the intensity of said first component of said received secondary light radiation,
   e. observing the positions in said area wherein said secondary light radiation was received, and
   f. repeating the aforesaid steps $(b) - (e)$.

2. A method as claimed in claim 1 wherein said primary light radiation is of a wavelength composition such as to excite bioluminescence in micro-organisms suspended in said zones.

3. A method as claimed in claim 2 wherein said primary light radiation comprises wavelengths of less than about 3,500 A and wherein said zones are located less than about 10 cm. from the surface of sea.

4. A method as claimed in claim 1 wherein said primary light radiation comprises wavelengths of the visible range and wherein said zones are located less than about two meters from the surface of the sea.

5. A method as claimed in claim 1 wherein the first component of said secondary light radiation comprises a first portion consisting of light reflected from said sub-surface zones and a second portion consisting of bioluminescence, and wherein said method includes the step of separately determining the respective intensities of the first and second portions of said first component of said secondary light radiation.

* * * * *